(12) United States Patent
Insel et al.

(10) Patent No.: US 8,114,590 B2
(45) Date of Patent: *Feb. 14, 2012

(54) DIAGNOSIS AND TREATMENT OF CHRONIC LYMPHOCYTIC LEUKEMIA (CLL)

(75) Inventors: Paul A. Insel, Atlanta, GA (US); Lingzhi Zhang, San Diego, CA (US); Fionna Murray, San Diego, CA (US); Joan R. Kanter, Imperial Beach, CA (US); Thomas Kipps, Rancho Santa Fe, CA (US); Laura Rassenti, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/960,955

(22) Filed: Dec. 6, 2010

(65) Prior Publication Data

US 2011/0117562 A1  May 19, 2011

Related U.S. Application Data

(63) Continuation of application No. 12/096,628, filed as application No. PCT/US2006/061727 on Dec. 7, 2006, now Pat. No. 7,846,664.

(60) Provisional application No. 60/748,253, filed on Dec. 7, 2005.

(51) Int. Cl.
*C12Q 1/68* (2006.01)
*C07H 21/04* (2006.01)

(52) U.S. Cl. .................. 435/6; 536/24.31; 536/24.33
(58) Field of Classification Search .................. None
See application file for complete search history.

(56) References Cited

U.S. PATENT DOCUMENTS

| | | | |
|---|---|---|---|
| 6,020,135 A | 2/2000 | Levine et al. | |
| 6,818,651 B2 | 11/2004 | Weinbrenner et al. | |
| 6,849,638 B2 | 2/2005 | Stolle et al. | |
| 2004/0018513 A1 | 1/2004 | Downing et al. | |

OTHER PUBLICATIONS

Moon et al., 2002, "Inhibition of PDE3B Augments PDE4 Inhibitor-Induced Apoptosis in a Subset of Patients with Chronic Lymphocytic Leukemia," Clinical Cancer Research, vol. 8, 589-595.

*Primary Examiner* — Amy Bowman
(74) *Attorney, Agent, or Firm* — Sutherland Asbill & Brennan LLP

(57) ABSTRACT

The present invention provides diagnostic methods and kits for diagnosis of chronic lymphocytic leukemia (CLL) by determining expression levels of isoforms of cyclic nucleotide phosphodiesterases (PDEs) associated with CLL, particularly, PDE7B and/or PDE3B, and a ratio of mRNA expression of PDE7B to PDE3B. The present invention provides that CLL lymphocytes uniformly expressed high levels of PDE7B and low levels of PDE3B relative to those of normal lymphocytes. A method of treatment and a pharmaceutical composition for CLL comprising one or more therapeutic agents capable of modulating expression or activity levels of isoforms of PDEs associated with CLL, and/or reversing the ratio of PDE7B/PDE3B mRNA expression levels are also provided.

10 Claims, 6 Drawing Sheets

DIAGNOSIS AND TREATMENT OF CHRONIC LYMPHOCYTIC LEUKEMIA (CLL)

CROSS-REFERENCE TO RELATED APPLICATIONS

The present application is a continuation application of U.S. application Ser. No. 12/096,628, now U.S. Pat. No. 7,846,664, which claims priority to PCT Application No. PCT/US2006/061727, which claims priority to U.S. Provisional Patent Application Ser. No. 60/748,253 filed Dec. 7, 2005, the entire contents of which are hereby incorporated by reference.

STATEMENT OF GOVERNMENT INTEREST

The invention was made with government support under Grant No. 5R01 GM61774-04 awarded by the National institutes of Health and the National Institute of General Medical Sciences. The government has certain rights in this invention.

FIELD OF THE INVENTION

The present invention relates to methods for diagnosis and treatment of chronic lymphocytic leukemia (CLL). More particularly, the present invention relates to isoforms of cyclic nucleotide phosphodiesterase (PDE) in relation to CLL, and method of use thereof, for diagnosis and treatment of CLL.

BACKGROUND OF THE INVENTION

Chronic lymphocytic leukemia (CLL), a cancer of the white blood cells and bone marrow, is characterized by uncontrolled proliferation and/or reduced cell death (apoptosis) of blood cells, specifically the B lymphocytes, and is the most widespread form of adult leukemia. Many cases of CLL are detected by routine blood tests in persons with no symptoms, however, patients may have enlarged lymph nodes, enlarged liver and spleen, fatigue, bone pain, excessive sweating, loss of appetite, weight loss, flank pain, and generalized itching. Abnormal bruising, which is a more well known symptom of CLL, often does not appear until late in the illness. CLL affects the B lymphocytes (antibody producing cells) and causes suppression of the immune system, failure of the bone marrow, and infiltration of malignant cells into organs. Although CLL starts in the bone marrow, it can spread to the blood, lymph nodes, spleen, liver, central nervous system (CNS), and other organs. It does not usually form a solid mass or tumor.

The hallmark of CLL is sustained, absolute lymphocytosis (>10,000/μL) and increased lymphocytes (>30%) in the bone marrow. At diagnosis, uncommonly, there may be moderate anemia and thrombocytopenia because of bone marrow infiltration, splenomegaly, or immunohemolytic anemia and thrombocytopenia. Some patients will have hypogammaglobulinemia, and occasionally a monoclonal serum immunoglobulin spike of the same type may be found on the leukemic cell surface.

In an asymptomatic patient, CLL may be diagnosed from abnormal blood counts. Otherwise, CLL should be suspected in a patient with insidious onset of the nonspecific features mentioned above who has generalized lymphadenopathy. CLL is diagnosed by an increase in lymphocytosis and/or bone marrow infiltration coupled with the characteristic features of morphology and immunophenotype, which confirm the characteristic clonal population. Reactive lymphocytosis associated with viral infections can be differentiated by the clinical picture and the presence of atypical lymphocytes on blood smear. Confusion with other diseases may be avoided by determination of cell surface markers. For instance, CLL lymphocytes coexpress the B-cell antigens CD19 and CD20 along with the T-cell antigen. CLL B cells express relatively low levels of surface-membrane immunoglobulin (compared with normal peripheral blood B cells) and a single light chain (kappa or lambda). The cells in B-cell CLL also co-express B-cell markers, such as CD5, CD9, and CD23 (1).

Clinical staging is primarily based on hematologic changes or extent of disease, and is useful for prognosis and treatment. Accepted treatment regimens for patients with CLL consist of administration of a variety of therapeutic anti-CLL agents, including nucleoside analogs or alkylating agents, and current trials are investigating the benefits of combinations of these agents with monoclonal antibodies. However, therapeutic options for patients with CLL are limited, and in most cases, are ineffective or have a limited period of effectiveness. Relapse of the disease often occurs and these patients acquire resistance, not only to the drug used for patient treatment, but to other drugs as well.

The therapeutic approaches for CLL aim to induce or increase apoptosis of malignant B-cells. The second messenger cAMP can promote apoptosis via activation of protein kinase A (PKA) in malignant B- and T-cells; pharmacological agents that increase cAMP levels thus have the potential to treat CLL (2-4). The intracellular concentration of cAMP and PKA activity are lower in lymphocytes of CLL patients than in those of normal subjects, suggesting a disease-related defect in this pathway (5, 6).

The cellular level of cAMP is governed by the balance between its formation by adenylyl cyclases (ACs) and degradation by cyclic nucleotide phosphodiesterases (PDEs). Eleven families of PDEs that hydrolyze cAMP and cGMP have been characterized and are comprised of a number of isoforms and splice variants (7). For instance, PDE4, 7, and 8 isoforms are specific for cAMP; PDE5, 6, and 9 isoforms are specific for cGMP; and PDE1, 2, 3, 10, and 11 isoforms have dual specificity. Members of the same PDE family show 65% or greater amino acid sequence identity, whereas between families the amino acid identity drops to 40% or lower (23, 49-50). Different PDEs can be distinguished from each other by their structure, tissue expression, localization, substrate specificity, regulation, and sensitivity to PDE inhibitors (23, 50).

PDEs have unique regulatory characteristics, cellular distribution, subcellular localization and sensitivities to inhibitors that make them attractive drug targets for specific diseases. Previous studies have shown that the nonselective PDE inhibitor theophylline increases intracellular cAMP and induces apoptosis in peripheral blood mononuclear cells (PBMC) of CLL patients without affecting normal B-cells and down-regulates expression of the anti-apoptotic protein Bcl-2 in CLL-PBMC (8, 9). Addition of theophylline to chlorambucil (an alkylating agent commonly used to treat CLL) can increase the response rate and progression-free survival of CLL patients (10, 11). Because theophylline inhibits many PDEs and has a narrow therapeutic index, treatment of CLL might be aided by the identification of a PDE isoform that could be targeted for its pro-apoptotic effect in this disease.

PBMC isolated from CLL patients expresses numerous PDEs, including PDE4 isoforms that are constitutively expressed. PDE4-specific inhibitors can induce apoptosis of CLL-PBMC and to augment killing of such cells by glucocorticoids, a clinical therapy in CLL (3, 4, 13). Akin to theophylline, PDE4 inhibitors can decrease the expression of anti-apoptotic proteins (e.g., Bcl-2) and enhance expression of the pro-apoptotic protein Bax in CLL-PBMC (14). Such results suggest that PDE4 inhibitors are a potential therapy for CLL but other PDE isoforms may be a more unique targets for this disease.

PDE7 is also found to play a role in the activation and/or proliferation of T cells (27), and isoform PDE7A has been cloned and detected in lymphoid cells (B and T lymphocytes) from patients with CLL (22-23). PDE7A further has two isoforms generated by alternate splicing: PDE7A1 restricted mainly to T cells and the brain, and PDE7A2 for which mRNA is expressed in a number of cell types including muscle cells. The isoforms have different sequences at the amino termini, and it is thought that this portion of each molecule is likely to be important for cellular localization of the enzyme. However, the catalytic domain of each PDE7A enzyme is identical (51). Isoform PDE7B has also been cloned (23, 28, 52) showing approximately 70% homology to PDE7A in the catalytic domain (52). Expression of PDE7B was detected in multiple tissues, including brain, heart, pancreas, liver, and skeletal muscle, but not in lymphoid cells.

CLL is a heterogeneous disorder whose course in individual patients is quite variable (33, 34). Methods used to assess prognosis in CLL do not consistently identify stable vs. progressive forms of the disease therefore new prognostic markers could prove useful (35, 36). WBC, lymphocyte doubling time (<12 months indicating poor prognosis), and factors that include serum constituents (e.g., thymidine kinase, LDH, soluble CD23, $\beta_2$-microglobulin), and features of CLL cells (e.g., p53-mutations, CD38 expression, somatic mutations in IgVH, and ZAP-70 expression) have been studied as predictors of outcome in CLL-patients (34, 37, 38-44). Unfortunately methods for measuring all such factors are not standardized and are not available in every clinical laboratory (45).

Therefore, there is a need to discover new diagnostic methods by identifying new biomarker and/or prognostic factors associated with CLL, and therapies for CLL in order to make significant progress in improving overall patient condition and survival in this disease. Given the fact that previous studies have not comprehensively compared the expression of PDE isoforms in CLL patients, it would be important and valuable to examine the expression or enzyme activities of PDE isoforms, in particular isoforms that hydrolyze cAMP, in CLL-PBMC, and further, to investigate if their inhibition would promote apoptosis in these cells. Thus, selective PDE isoforms may serve as novel biomarkers for CLL and even provide new therapeutic targets, inhibition of which would have greater efficacy to specifically kill malignant B-cells and further treating and/or curing CLL.

SUMMARY OF THE INVENTION

The present invention provides a diagnostic method for chronic lymphocytic leukemia (CLL). Such method comprises the steps of: (a) determining in a sample from a patient an expression level of an isoform of phosphodiesterase (PDE) associated with CLL, (b) comparing the patient's expression level to the expression level of the isoform of PDE associated with CLL in a normal subject, and (c) diagnosing said patient as at risk for CLL when the patient's expression level is significantly increased or decreased compared to said normal subject's expression level. In one preferred embodiment, the isoform of PDE associated with CLL is phosphodiesterase 7B (PDE7B). In another preferred embodiment, the isoform of PDE associated with CLL is phosphodiesterase 3B (PDE3B).

Other PDE isoforms associated with CLL can also be included in the present invention. In yet another preferred embodiment, the sample from a patient used for the diagnosis of CLL comprises lymphocytes that include, but are not limited to peripheral blood mononuclear cells (PBMCs) or B cells.

The present invention provides that both PDE7B mRNA and protein expression levels in CLL patients are significantly increased as compared to those in normal subjects. In one preferred embodiment, the present invention provides that PDE7B mRNA and protein expression levels in CLL patients are about 5-70 fold increased, and 5-90 fold increased, respectively, as compared to those in normal subjects.

The present invention also provides that both PDE3B mRNA and protein expression levels in CLL patients are significantly decreased as compared to those in normal subjects. In one preferred embodiment, the present invention provides that PDE3B mRNA expression levels in CLL patients are about 20-fold decreased compared to those in normal subjects.

The diagnostic method of the present invention further comprises a step of determining a ratio of PDE7B to PDE3B mRNA expression levels. In one preferred embodiment, the present invention provides that the ratio of PDE7B to PDE3B mRNA expression levels in CLL patients is significantly increased as compared to that in normal subjects. In yet another preferred embodiment, the present invention provides that the ratio of PDE7B/PDE3B mRNA expression levels in CLL patients is about 10-1000-fold increased compared to that in normal subjects. In yet another preferred embodiment, the present invention provides that the ratio of PDE7B/PDE3B mRNA expression levels in normal subjects is less than 0.3, whereas the ratio of PDE7B/PDE3B mRNA expression levels in CLL patients is greater than 3.

The present invention further provides a kit for a diagnosis of CLL. The kit comprises biomarker detecting reagents for determining a differential expression level of isoforms of PDE and instructions for their use in diagnosing CLL. In certain preferred embodiments, the isoforms of PDE include, but are not limited to, PDE7B and PDE3B. In other preferred embodiments, the kit comprises biomarker detecting reagents suitable for determining both mRNA and/or protein expression levels of PDE isoforms, including, but not limited to, PDE7B and/or PDE3B. In yet other preferred embodiments, the kit of the present invention comprises means for calculating the ratio of PDE7B to PDE3B mRNA expression levels. In yet another preferred embodiments, the instructions in the kit of the present invention indicate that the ratio of PDE7B/PDE3B mRNA expression levels in normal subjects is less than 0.3, whereas the ratio of PDE7B/PDE3B mRNA expression levels in CLL patients is greater than 3.

The present invention further provides a method of a treatment comprising administering to a patient in need thereof a biologically effective amount of one or more therapeutic agents capable of directly or indirectly modulating expression or activity levels of one or more PDE isoforms associated with CLL. Such PDE isoforms associated with CLL include but are not limited to PDE7B and/or PDE3B. In one preferred embodiment, the PDE isoform is PDE7B. In yet another preferred embodiment, the PDE isoform is PDE3B. In further certain preferred embodiments, the present invention provides that the therapeutic agents are capable of directly or indirectly inhibiting PDE7B mRNA and/or protein expressions or enzyme activity in CLL lymphocytes. In yet other preferred embodiments, the therapeutic agents comprises oligonucleotides, antisense oligonucleotides, polynucleotides, therapeutic DNA, ribozymes, dsRNAs, siRNA, RNAi, or gene therapy vectors that are capable of inhibiting PDE7B mRNA and/or protein expressions in CLL lymphocytes. In yet other preferred embodiments, the therapeutic agents comprises PDE7, preferably PDE7B, inhibitors, antagonists, antibodies or other immunologically active molecules that immunoreact with these enzymes, resulting in apoptosis of CLL lymphocytes. In yet another preferred embodiment, the therapeutic agent is selective PDE7, preferably PDE7B, inhibitors. In yet other certain preferred embodiments, the therapeutic agents can be any drugs, compounds, small molecules, proteins, antibodies, nucleotides, and the like, that are capable of reversing the ratio of PDE7B/PDE3B expression levels in CLL lymphocytes that include, but are not limited to PBMCs or B cells. Furthermore, the present invention provides a pharmaceutical composition for treating CLL comprising the therapeutic agents of the present invention, as described above.

BRIEF DESCRIPTION OF THE DRAWINGS

FIG. 1 illustrates that mRNA expression of multiple phosphodiesterase (PDE) isoforms are altered with chronic lymphocytic leukemia (CLL).

FIG. 2 shows that the mRNA expression of PDE7B is increased and PDE3B is decreased in CLL-PBMC as compared to normal-PBMC. PDE7B and PDE3B mRNA expression were assayed by QPCR.

FIG. 4 shows that the mRNA ratio of PDE7B/3B significantly correlates with WBC, percentage lymphocytes and CD38 but does not correlate with other prognostic factors for CLL. The Spearman test was used to analyze the relationship between the ratio of PDE7B/3B and other FACS and clinical data. All data available for the subjects was used to assess the correlation with PDE7B/3B and yielded the following p values.

FIG. 5 illustrates that PDE7B protein expression and the contribution of PDE7 to total cAMP-PDE activity are increased in CLL-PBMC compared to normal-PBMC. FIG. 6 shows that the PDE7 inhibitor BRL-50481 dose-dependently induces apoptosis in CLL-PBMC, but not in normal-PBMC. Apoptosis was assessed in PBMC from 6 normal subjects (FIG. 6A) and CLL patients (FIG. 6B) by staining with Annexin V and analyzed by flow cytometry after 72 hrs incubation of vehicle alone (Control), or the PDE7 inhibitor BRL-50481 at 10 µM (BRL 10), 30 µM (BRL30) and 100 µM (BRL100). Because of differences in "basal apoptosis" of the vehicle alone (control) in different individuals (FIGS. 6A and 6B), results were analyzed as % apoptotic cells relative to control for each concentration of BRL-50481 (FIG. 6C). Each data point represents mean+/−SE of 6 normal subjects and 10 B-CLL patients. *, $P<0.05$, **$P<0.01$ compared to vehicle.

DETAILED DESCRIPTION OF THE INVENTION

The present invention may be understood more readily by reference to the following detailed description of the preferred embodiments of the invention and the Examples included herein. However, before the present peptides, compounds, compositions, and methods are disclosed and described, it is to be understood that this invention is not limited to specific nucleic acids, specific peptides or proteins, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. It is also to be understood that as used in the specification and in the claims, "a" or "an" can mean one or more, depending upon the context in which it is used. Thus, for example, reference to "a cell" can mean that at least one cell can be utilized.

The present invention provides a diagnostic method for chronic lymphocytic leukemia (CLL). Such method comprises the steps of (a) determining in a sample from a patient an expression level of an isoform of phosphodiesterase (PDE) associated with CLL, (b) comparing the patient's expression level to the expression level of the isoform of PDE associated with CLL in a normal subject, and (c) diagnosing said patient as at risk for CLL when the patient's expression level is significantly increased or decreased compared to said normal subject's expression level. As used herein, the term "isoform" (also known as an isozyme if the protein is an enzyme) refers to proteins and/or enzymes with same or similar function but which differ in amino acid and/or nucleotide sequences. Isoforms exist by multiple mechanisms, such as different gene loci, multiple alleles (also called allelomorphs, allelozymes, or allozymes), different subunit interaction, different splice forms, or different post-translational modification, and can usually be separated by electrophoresis or some other separation technique known in the art.

As used herein, the term "phosphodiesterase (PDE)" includes cyclic nucleotide phosphodiesterases (PDEs) that hydrolyze cAMP and cGMP. Eleven families of PDEs (PDE1-11) are now known including, but not limited to their isoforms, homologs and splice variations, now known, or later described. In addition, as used herein, the term "isoform of PDE" includes, now known, or later described, enzymes that contain one or more PDE core domains including any functional domains/motifs and having cAMP and/or cGMP hydrolysis activities, with or without one or more mutations, deletions or insertions. As used herein, the term "associated with CLL" means that expression levels of an isoform of PDE in a subject at risk for CLL is significantly and/or substantially different from that in a normal subject. As used herein, the term "significantly and/or substantially different" means statistically different, wherein the difference is subject to any statistic analysis with a P value of less than 0.05, preferably less than 0.01, more preferably less than 0.001.

In one preferred embodiment, the isoform of PDE is PDE7B. In another preferred embodiment, the isoform of PDE is PDE3B. As used herein, the term PDE7B and/or PDE3B refers to PDE7B or PDE3B proteins, their isoforms or homologs having at least 60% homologous, preferably 75% homologous, more preferably 85%, 90%, 95%, 96%, 97%, 98%, 99% or more homologous, to a wild type PDE7B or PDE3B protein core domains. As used herein, the PDE7B or PDE3B protein core domains comprise biologically active portions of the proteins. As used herein, the "biologically active portions" of PDE7B or PDE3B proteins include one or more fragments of the proteins comprising amino acid sequences sufficiently homologous to, or derived from, the amino acid sequence of the proteins, which include fewer amino acids than the full length protein, and exhibit at least one activity of the full-length proteins. Typically a biologically active portion comprises a domain or motif with at least one activity of the protein. A biologically active portion of a protein can be a polypeptide which is, for example, 10, 25, 50, 100, 200 or more amino acids in length. In one embodiment, a biologically active portion of these proteins can be used as a target for developing agents which modulate activities of these proteins.

Moreover, the PDE7B and/or PDE3B used herein include PDE proteins and/or enzymes encoded by polynucleotides that hybridize to the polynucleotide encoding these proteins under stringent conditions. As used herein, "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under different stringent conditions. The present invention includes polynucleotides capable of hybridizing under reduced stringency conditions, more preferably stringent conditions, and most preferably highly stringent conditions, to polynucleotides encoding PDE7B and/or PDE3B protein described herein. As used herein, the term "stringent conditions" refers to hybridization overnight at 60° C. in 10× Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in a preferred embodiment, the phrase "stringent conditions" refers to hybridization in a 6×SSC solution at 65° C. In another embodiment, "highly stringent conditions" refers to hybridization overnight at 65° C. in 10× Denhart's solution, 6×SSC, 0.5% SDS and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are described in Meinkoth and Wahl, 1984, Anal. Biochem. 138:267-284; Current Protocols in Molecular Biology, Chapter 2, Ausubel et al., eds., Greene Publishing and Wiley-Interscience, New York, 1995; and Tijssen, 1993, Laboratory Techniques in Biochemistry and Molecular Biology: Hybridization with Nucleic Acid Probes, Part 1, Chapter 2, Elsevier, New York, 1993.

Furthermore, the PDE7B and/or PDE3B proteins used herein can also be chimeric protein or fusion protein. As used herein, a "chimeric protein" or "fusion protein" comprises a first polypeptide operatively linked to a second polypeptide. Chimeric proteins may optionally comprise a third, fourth or fifth or other polypeptide operatively linked to a first or second polypeptide. Chimeric proteins may comprise two or more different polypeptides. Chimeric proteins may comprise multiple copies of the same polypeptide. Chimeric proteins may also comprise one or more mutations in one or more of the polypeptides. Methods for making chimeric proteins are well known in the art.

As used herein, the term "expression level" refers to an amount of a gene and/or protein that is expressed in a cell. As used herein, a "gene" includes a polynucleotide containing at least one open reading frame that is capable of encoding a particular polypeptide or protein after being transcribed and translated. Any of the polynucleotide sequences described herein may also be used to identify larger fragments or full-length coding sequences of the gene with which they are associated. Methods of isolating larger fragment sequences are known to those of skill in the art.

As used herein, the terms "polynucleotide," "nucleic acid/nucleotide" and "oligonucleotide" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, DNA, cDNA, genomic DNA, recombinant polynucleotides, branched polynucleotides, plasmids, vectors, isolated DNA of any sequence, isolated RNA of any sequence, nucleic acid probes, and primers. Polynucleotides may be naturally-occurring, synthetic, recombinant or any combination thereof.

As used herein, a "naturally-occurring" polynucleotide molecule includes, for example, an RNA (mRNA) or DNA molecule having a nucleotide sequence that occurs in nature (e.g., encodes a natural protein). As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" also encompasses the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form. The "polynucleotide sequence" is the alphabetical representation of a polynucleotide molecule. A polynucleotide is composed of a specific sequence of four nucleotide bases: adenine (A); cytosine (C); guanine (G); thymine (T); and uracil (U) in place of guanine when the polynucleotide is RNA. This alphabetical representation can be inputted into databases in a computer and used for bioinformatics applications such as, for example, functional genomics and homology searching.

As used herein, the term "protein" or "polypeptide" is interchangeable, and includes a compound of two or more subunit amino acids, amino acid analogs, or peptidomimetics. The subunits may be linked by peptide bonds. In another embodiment, the subunit may be linked by other bonds, e.g., ester, ether, etc. As used herein, the term "amino acid" includes either natural and/or unnatural or synthetic amino acids, including both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

The present invention provides a diagnostic method for CLL or other hematological disorders or malignancies by comparing expression levels of PDE isoforms in subjects at risk for such disorders vs. normal subjects. In certain preferred embodiments of the present invention, both PDE7B mRNA and protein expression levels in lymphocytes from a subject at risk for CLL are compared to a baseline level of PDE7B mRNA and protein expression levels in normal lymphocytes, wherein an elevated level of PDE7B mRNA and/or protein expression levels in relation to the baseline level of PDE7B mRNA and/or protein expression levels indicates an association with CLL in that subject. In yet other preferred embodiments of the present invention, both PDE3B mRNA and protein expression levels in lymphocytes from a subject at risk for CLL are compared to a baseline level of PDE3B mRNA and protein expression levels in normal lymphocytes, wherein a decreased level of PDE3B mRNA and/or protein expression levels in relation to the baseline level of PDE3B mRNA and/or protein expression levels indicates an association with CLL in the subject. The diagnostic method of the present invention is performed using any tissue containing lymphocytes, including but not limited to spleen, lymph nodes, bone marrow, lymph, a whole blood sample from the subject or a whole blood sample that has been treated and processed to isolate the peripheral blood mononuclear cells ("PBMC"), B-cells, T-cells, or other lymph cells.

The present invention provides that both PDE7B mRNA and protein expression levels in CLL patients are significantly increased compared to those in normal subjects. In one preferred embodiment, the PDE7B mRNA expression level in CLL patients is about 5-70 fold increased compared to that in normal subjects. Preferably, PDE7B mRNA expression level is 5-, 10-, 20-, 30-, 40-, 50-, 60-, and 70-fold higher than that in normal subjects. In yet another preferred embodiment, the PDE7B protein expression level in CLL patients is about 5-90 fold increased compared to that in normal subjects. Preferably, PDE7B protein expression level is 5-, 10-, 15-, 20-, 30-, 40-, 50-, 60-, 70-, 80, and 90-fold higher than that in normal subjects.

Contrary, in yet another preferred embodiment, both PDE3B mRNA and protein expression levels in CLL patients are significantly decreased compared to those in normal subjects. In one preferred embodiment, the PDE3B mRNA expression levels in CLL patients are 0.003-0.137, about 20-fold lower than those in normal subjects.

The diagnostic method of the present invention further comprising a step of determining a ratio of PDE7B/PDE3B mRNA expression levels, which is significantly increased in CLL patients compared to that in normal subjects. In one preferred embodiment, the present invention provides that the average PDE7B/PDE3B mRNA ratio is about 1000-fold higher in CLL patients than that in normal subjects. Preferably, the PDE7B/PDE3B mRNA ratio is about 3-, 10-, 30-, 100-, 200-, 300-, 400-, 500-, 600-, 700-, 800-, 900-, and 1000-fold higher in CLL patients than that in normal subjects. Accordingly, the present invention provides a method for diagnosis of CLL by measuring the PDE7B/3B mRNA ratio, which is over 3 to diagnose CLL, and under 0.3 for normal.

The present invention further provides a kit for a diagnosis of CLL comprising biomarker detecting reagents for determining expression levels of isoforms of PDEs, and instructions for their use in diagnosing CLL. As used herein, the term "biomarker" refers to an indicator and/or prognostic factor of biologic or pathologic processes or pharmacologic responses to a therapeutic intervention. As used herein, the term "prognostic factor" refers to any molecules and/or substances contributing to a predicted and/or expected course of CLL including various developments, changes and outcomes of the disease. As used herein, the term "detecting reagents" refer to any substances, chemicals, solutions used in chemical reactions and processes that are capable of detecting, measuring, and examining PDEs and their isoforms of interest. In certain preferred embodiments, the isoforms of PDEs include, but are not limited to, PDE7B and PDE3B. In other preferred embodiments, the biomarker detecting reagents used herein comprise chemicals, substances, and solutions that are suitable for determining either mRNA or protein, or both expression levels of PDEs and their isoforms, including, but not limited to, PDE7B and/or PDE3B.

One of the detecting reagents may include immunologically active molecules comprising an antibody molecule or a fragment thereof that specifically binds to PDEs and their isoforms or an antigen for PDEs and their isoforms. The term "antibody" as used herein encompasses monoclonal antibodies (including full length monoclonal antibodies), polyclonal antibodies, multispecific antibodies (e.g., bispecific antibodies), and antibody fragments so long as they exhibit the desired biological activity of binding to PDEs and their isoforms of interest. The term "antibody fragments" comprise a portion of a full length antibody, generally the antigen binding or variable region thereof. Examples of antibody fragments include Fab, Fab', F(ab')², and Fv fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The "monoclonal antibodies" may also be isolated from phage antibody libraries using the techniques known in the art.

The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

The term "single-chain Fv" or "sFv" antibody fragments comprise the VH and VL domains of antibody, wherein these domains are present in a single polypeptide chain. Generally, the Fv polypeptide further comprises a polypeptide linker between the VH and VL domains which enables the sFv to form the desired structure for antigen binding.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-polyacrylamide gel electrophoresis under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

In order to avoid potential immunogenicity of the monoclonal antibodies in human, the monoclonal antibodies that have the desired function are preferably humanized. "Humanized" forms of non-human (e.g., murine) antibodies are chimeric antibodies that contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. Antibodies capable of immunoreacting to particular PDEs and their isoforms are made using conventional methods known in the art.

Other molecules which selectively bind to PDEs and their isoforms of interest or their gene products (e.g. mRNAs) known to those skilled in the art, or discovered in the future are contemplated within the scope of the present invention. Such molecules include primers and/or probes comprising desired DNA, RNA, and/or DNA/RNA hybrid sequences. As used herein, the term "primer" refers to a segment of DNA or RNA that is complementary to a given DNA or RNA sequences (e.g. sequences of a particular PDE or its isoform) and that is needed to initiate replication by DNA polymerase, and a term "probe" refers to a substance, such as DNA, that is radioactively labeled or otherwise marked and used to detect or identify another substance in a sample. As used herein, the term "primer" and "probe" are used interchangeably, and typically comprise a substantially isolated oligonucleotide typically comprising a region of nucleotide sequence that hybridizes under stringent conditions to at least about 12, preferably about 25, more preferably about 40, 50, or 75 consecutive nucleotides of a sense and/or an antisense strands of a nucleotide sequence of PDEs and their isoforms of interest; or naturally occurring mutants thereof. As used herein, primers based on the nucleotide sequence of PDEs and their isoforms of interest can be used in PCR reactions to clone homologs of these PDEs and their isoforms. Probes based on the nucleotide sequences of these PDEs and their isoforms can be used to detect transcripts or genomic sequences encoding the same or substantially identical polypeptides or proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express or over-express these PDEs and/or their isoforms, such as by measuring a level of encoding nucleic acid, in a sample of cells, e.g., detecting mRNA levels or determining whether a genomic gene has been mutated or deleted.

In certain preferred embodiments, the biomarkers and/or prognostic factors for diagnosing and monitoring CLL comprise PDE7B, PDE3B, and ratio of PDE7B/3B. In yet certain preferred embodiments, the kit of the present invention comprise any detecting reagents that are capable to detect mRNA, protein, or both, expression levels of PDE7B and/or PDE3B. In yet another preferred embodiment, the kit of the present invention comprise means for calculating the expression ratio of two or more PDE isoforms, preferably, the expression ratio of PDE7B to PDE3B. The kit of the present invention further comprises an instruction for use in diagnosing and monitoring CLL. In one preferred embodiment, the instruction in the kit provides that an elevated PDE7B mRNA and/or protein expression levels, or a decreased PDE3B mRNA and/or protein expression levels indicates an association with CLL. In yet another preferred embodiment, the instruction in the kit provides that an elevated PDE7B/PDE3B mRNA ratio also indicates an association with CLL. Moreover, the instruction in the kit also provides that normal cells have the PDE7B/3B mRNA ratio under 0.3, while CLL cells have the PDE7B/3B mRNA ratio above 3.

Furthermore, the present invention provides a method for treating CLL by administering to a CLL patient a biologically effective amount of one or more therapeutic agents capable of directly or indirectly modulating expression or activity level of one or more PDEs and/or their isoforms associated with CLL. As used herein, the term "biologically effective amount" or "therapeutically effective amount" of therapeutic agent is intended to mean a nontoxic but sufficient amount of such therapeutic agents to provide the desired therapeutic effect. The amount that is effective will vary from subject to subject, depending on the age and general condition of the individual, the particular active agent or agents, and the like. Thus, it is not always possible to specify an exact effective amount. However, an appropriate effective amount in any individual case may be determined by one of ordinary skill in the art using routine experimentation.

As used herein, the term "modulating" refers to up-regulation, induction, stimulation, potentiation, and/or relief of inhibition, as well as inhibition, attenuation and/or down-regulation or suppression. Inhibitors or antagonists are compounds that, e.g., bind to, partially or totally block stimulation, decrease, prevent, delay activation, inactivate, desensitize, or down regulate genes or proteins of PDEs and/or isoforms, e.g., PDE7B Activators or agonists are compounds that, e.g., bind to, stimulate, increase, open, activate, facilitate, enhance activation, sensitize, or up regulate gene or proteins of PDEs and/or isoforms, e.g., PDE3B.

As used herein, the term "therapeutic agents" may refer to any oligonucleotides (antisense oligonucleotide agents), polynucleotides (e.g. therapeutic DNA), ribozymes, dsRNAs, siRNA, RNAi, and/or gene therapy vectors. The term "antisense oligonucleotide agent" refers to short synthetic segments of DNA or RNA, usually referred to as oligonucleotides, which are designed to be complementary to a sequence of a specific mRNA to inhibit the translation of the targeted mRNA by binding to a unique sequence segment on the mRNA. Antisense oligonucleotides are often developed and used in the antisense technology. The term "antisense technology" refers to a drug-discovery and development technique that involves design and use of synthetic oligonucleotides complementary to a target mRNA to inhibit production of specific disease-causing proteins. Antisense technology permits design of drugs, called antisense oligonucleotides, which intervene at the genetic level and inhibit the production of disease-associated proteins. Antisense oligonucleotide agents are developed based on genetic information.

As an alternative to antisense oligonucleotide agents, ribozymes or double stranded RNA (dsRNA), RNA interference (RNAi), and/or small interfering RNA (siRNA), can also be used as therapeutic agents for regulation of gene expression in cells. As used herein, the term "ribozyme" refers to a catalytic RNA-based enzyme with ribonuclease activity that is capable of cleaving a single-stranded nucleic acid, such as an mRNA, to which it has a complementary region. Ribozymes can be used to catalytically cleave target mRNA transcripts to thereby inhibit translation of target mRNA. The term "dsRNA," as used herein, refers to RNA hybrids comprising two strands of RNA. The dsRNAs can be linear or circular in structure. The dsRNA may comprise ribonucleotides, ribonucleotide analogs, such as 2'-O-methyl ribosyl residues, or combinations thereof. The term "RNAi" refers to RNA interference or post-transcriptional gene silencing (PTGS). The term "siRNA" refers to small dsRNA molecules (e.g., 21-23 nucleotides) that are the mediators of the RNAi effects. RNAi is induced by the introduction of long dsRNA (up to 1-2 kb) produced by in vitro transcription, and has been successfully used to reduce gene expression in variety of organisms. In mammalian cells, RNAi uses siRNA (e.g. 22 nucleotides long) to bind to the RNA-induced silencing complex (RISC), which then binds to any matching mRNA sequence to degrade target mRNA, thus, silences the gene.

As used herein, the therapeutic agents may also include any vectors/virus used for gene therapy. The term "gene therapy" refers to a technique for correcting defective genes or inhibiting or enhancing genes responsible for disease development. Such techniques may include inserting a normal gene into a nonspecific location within the genome to replace a nonfunctional gene; swapping an abnormal gene for a normal gene through homologous recombinants, repairing an abnormal gene to resume its normal function through selective reverse mutation; and altering or regulating gene expression and/or functions of a particular gene. As used herein, a term "vector/virus" refers to a carrier molecule that carries and delivers the "normal" therapeutic gene to the patient's target cells. Because viruses have evolved a way of encapsulating and delivering their genes to human cells in a pathogenic manner, most common vectors for gene therapy are viruses that have been genetically altered to carry the normal human DNA. As used herein, the viruses/vectors for gene therapy include retroviruses, adenoviruses, adeno-associated viruses, and herpes simplex viruses. The term "retrovirus" refers to a class of viruses that can create double-stranded DNA copies of their RNA genomes, which can be further integrated into the chromosomes of host cells, for example, Human immunodeficiency virus (HIV) is a retrovirus. The term "adenovirus" refers to a class of viruses with double-stranded DNA genomes that cause respiratory, intestinal, and eye infections in humans, for instance, the virus that cause the common cold is an adenovirus. The term "adeno-associated virus" refers to a class of small, single-stranded DNA viruses that can insert their genetic material at a specific site on chromosome 19. The term "herpes simplex viruses" refers to a class of double-stranded DNA viruses that infect a particular cell type, neurons. Herpes simplex virus type 1 is a common human pathogen that causes cold sores.

In certain preferred embodiments, the present invention provides a method of treating CLL using protein inhibitors, ligands, and/or antagonists and their pharmaceutical compositions that directly or indirectly inhibit PDE7B mRNA and protein expressions or enzyme activity in CLL lymphocytes. Such PDE7B selective inhibitors, ligands, antagonists comprise any polypeptides, proteins, synthesic, non-toxic, bioactive molecules, and/or immunologically active molecules that are capable of directly or indirectly inhibiting lymphocyte proliferation or promoting cell death by binding to PDE7B gene and/or protein and inhibiting the cAMP catabolism resulting in elevation of intracellular cAMP levels, and apoptosis of CLL lymphocytes.

In yet other certain preferred embodiments, the present invention provides a method of treating CLL using any drugs, compounds, small molecules, proteins, antibodies, nucleotides, and pharmaceutical compositions thereof, that are capable of reversing PDE7B/PDE3B mRNA ratio in CLL lymphocytes. As used herein, the term "pharmaceutical composition" contemplates compositions comprising one or more therapeutic agents as described above, and one or more pharmaceutically acceptable carriers or vehicles. As used herein, the term "pharmaceutically acceptable carriers or vehicles" comprises any acceptable materials, and/or any one or more additives known in the art. As used herein, the term "carriers" or "vehicle" refer to carrier materials suitable for drug administration through various conventional administration routes known in the art. Carriers and vehicles useful herein include any such materials known in the art, which are nontoxic and do not interact with other components of the composition in a deleterious manner.

The present invention also contemplates any conventional methods for formulation of pharmaceutical compositions as described above. Various additives, known to those skilled in the art, may be included in the formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

Throughout this application, various publications are referenced. The disclosures of all of these publications and those references cited within those publications in their entireties are hereby incorporated by reference into this application in order to more fully describe the state of the art to which this invention pertains.

Several examples are presented below. It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Material and Methods

Unless otherwise noted, all chemicals were purchased from Sigma-Aldrich. Cell culture reagents were obtained from Gibco (Gibco BRL, Grand Island, N.Y.).

PBMC isolation: Peripheral blood samples were collected from healthy blood donors (normal subjects) and CLL patients following informed consent, in agreement with institutional guidelines. The diagnosis of CLL was made by peripheral blood morphology and immunophenotyping. The patients' median age was 61 yr (range, 44-75 yr), with a median WBC of $142 \times 10^6$ cells/ml (range, 15 to $460 \times 10^6$ cells/ml). No patients had received cytoreductive chemotherapy. PBMC were isolated by density-gradient centrifugation using Ficoll-Paque (Amersham Biosciences), washed, and suspended in fetal-calf serum containing 10% DMSO before storing in liquid $N_2$ for subsequent use.

B cell isolation from normal subjects: B-cells were isolated from normal PBMC using magnetic beads coupled to CD19+ monoclonal antibodies (Dynal Biotech) and routinely resulted in >90% CD19+ cells, as assessed by flow cytometry.

Clinical Database: Clinical data including age, WBC, lymphocyte count, IgVH, and expression levels of ZAP-70, CD38 were collected with the use of the CRC information Management System, a 128-bit encrypted password-secured Web application. All activities regarding the use of patient data and samples followed or exceeded the guidelines set forth in the Health Insurance Portability and Accountability Act (15).

Reverse transcriptase PCR (RT-PCR) and Real-time PCR (QPCR): Total RNA was isolated from PBMC of CLL patients (n=24) and healthy donors (n=16) by use of Versagene RNA Cell Kit (Gentra, VWR) following the manufacturer's instructions. Superscript III First Strand Synthesis System (Invitrogen) was used to synthesize cDNA. Both PCR (MJ Research PTC-100 using Platinum Taq DNA polymerase) and Real-time PCR (MJ Research Opticon 2 using Eurogentec QPCR Mastermix Plus SYBR Green Kit) were performed using 2 to 8 ng RNA/reaction and 100 nM sense/antisense primers; two primer sets were designed for each PDE isoform.

One primer set has been previously published and the other set are available upon request (16). All primers were validated using human reference total RNA (Stratagene). Thermal cycling conditions were as follows: initial incubation of 10 min at 95° C. followed by 40 cycles of 15 s at 95° C., 30 s at 56° C., and 30 s at 72° C. All cDNA samples were run in duplicate. Samples were compared using the relative cycle threshold (Ct) method. The lower the Ct the greater the mRNA expression. Fold induction or repression was measured relative to the average in 16 normal subjects and calculated after normalizing to 28 s rRNA.

Western blot analysis: Western blot was performed on $\sim 5\text{-}10 \times 10^6$ cells/sample. Lysates were prepared using 50 mM Tris-HCl, 150 mM NaCl, 1% NP40, 0.5% sodium deoxycholate, and 0.1% SDS and protease inhibitors, separated by gel electrophoresis, immunoblotted using the NuPage gel system following the manufacturer's instructions (Invitrogen), and visualized by horseradish peroxidase and enhanced chemiluminescence (ECL Western blotting detection reagent; Amersham). Antibodies used were directed against PDE7B (Fabgennix) and $\beta$-actin (Abcam) as a loading control.

PDE activity assay: PDE activity was determined using 1 µM cyclic nucleotide as substrate via a two-step radioassay method adapted from a published procedure (17). In brief, substrate and protein were incubated over a period of time that PDE activity was linear, after which samples were boiled for 2 min. Results are calculated relative to the protein concentration. In order to identify the contribution of PDE7 to total PDE activity, the assay was preformed in the presence of the specific PDE7 inhibitor BRL-50481 [3-(N,N-dimethylsulfonamido)-4-methyl-nitrobenzene, TOCRIS).

Apoptosis: PBMC (1 million cells/ml) from B-CLL patients or normal subjects were cultured in RPMI media supplemented with 10% FBS, L-glutamine and penicillin/streptomycin at 37° C. in 5% $CO_2$ and treated with either vehicle or the PDE7 inhibitor BRL-50481 for 72 h. Apoptosis was assessed by flow cytometry as the percentage of cells stained with Annexin V and Propidium Iodide (PI) and analyzed by FACScan using CELLQuest software (Becton-Dickinson Immunocytometry System) (18).

Statistical Analyses: All determinations were performed in duplicate or triplicate, and each experiment was repeated at least three times. Values are expressed as mean±S.E. To determine statistical significance one-way ANOVA was performed followed by Bonferroni's post-hoc test. Comparison between two groups was based on an unpaired Students' t-test. A probability value of p<0.05 was considered to be statistically significant. The relationship between the ratio of PDE7B/3B and other CLL prognostic factors was analyzed using a one-tailed Spearman test.

Example 1

Figure 1A:
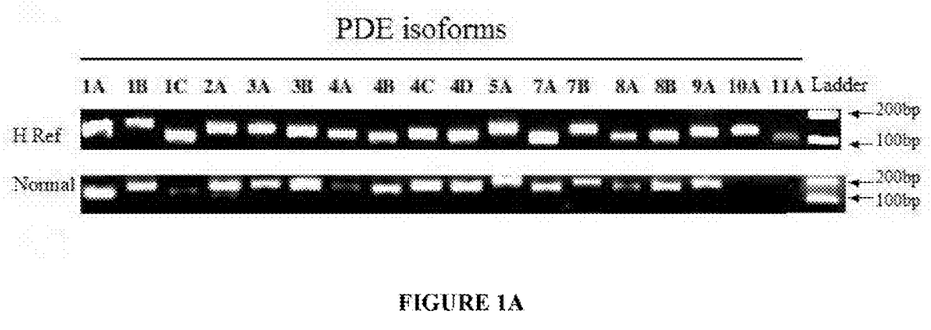
FIG. 1A illustrates representative RT-PCR of PDE isoforms expressed in Human reference RNA (upper panel) and normal-PBMC (lower panel).

PDE Isoforms Expression Profile in PBMCs from CLL Patients and Normal Subjects The mRNA expression of PDE isoforms were examined by RT-PCR and QPCR. Two sets of primers specific for 18 PDE isoforms and 28S rRNA (yielding either 100-200 bp or 300-400 bp PCR products) were validated against human QPCR reference total RNA (FIG. 1A shows a representative gel using the shorter set of primers). Using these primers, it was found that PBMC from normal subjects and CLL patients express mRNA for multiple PDE isoforms: PDE1A, 1B, 1C, 2A, 3A, 3B, 4A, 4B, 4C, 4D, 7A, 7B, 8A, 8B, and 9A (FIG. 1A-1B); mRNAs for PDE10A and PDE11A in normal- or CLL-PBMC were not detected in PBMCs from both normal subjects and CLL patients (FIG. 1A).

Figure 1B:
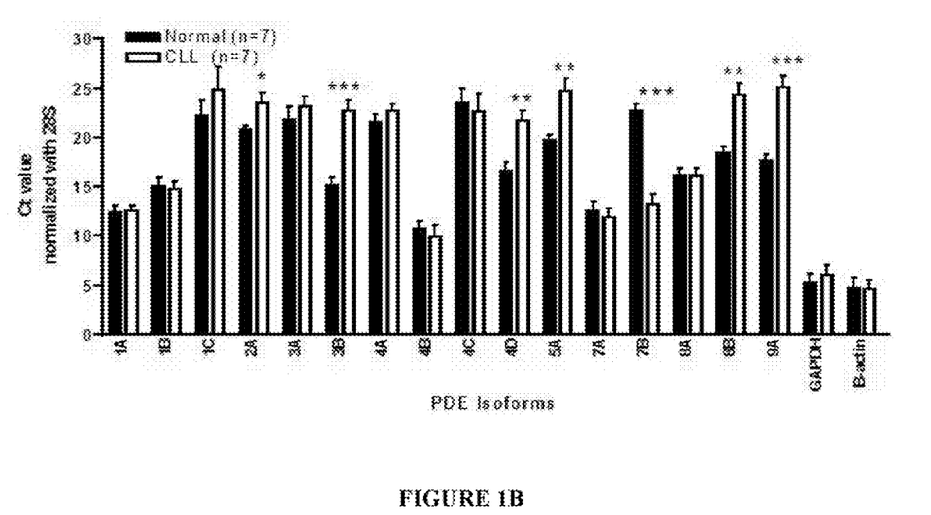
FIG. 1B shows QPCR analysis of the expression of PDE isoforms in PBMC from 7 normal subjects and 7 CLL patients. Data are expressed as Ct values normalized with 28S rRNA (mean+/−SE). Each patient's sample was repeated 4 times. *, $P<0.05$; , $P<0.01$; *$P<0.0001$, significant higher or lower of Ct value in CLL patients vs. normal subjects.

PBMCs from 7 CLL patients and 7 normal subjects were also tested using QPCR to determined if CLL was associated with altered PDE isoform expression. Although Ct can be influenced by primer efficiency, one can extrapolate quantitative information from Ct values for the PDE isoforms with low Ct corresponding to a high expression of a particular isoform. As shown in FIG. 1B, the principal PDEs expressed in normal- and CLL-PBMCs are PDE4B and PDE7A. QPCR revealed that CLL-PBMCs have increased expression of only PDE7B mRNA but show decreased mRNA expression of multiple PDEs: 2A, 3B, 4D, 5A, 8B and 9A. Because PDE3B was the only one that was consistently detectable and significantly decreased in PBMCs from CLL patient studied, further studies focused on the PDE7B and PDE3B isoforms.

Example 2

Increased PDE7B mRNA and Protein Expressions and PDE7 Activity with CLL

Figure 2A:
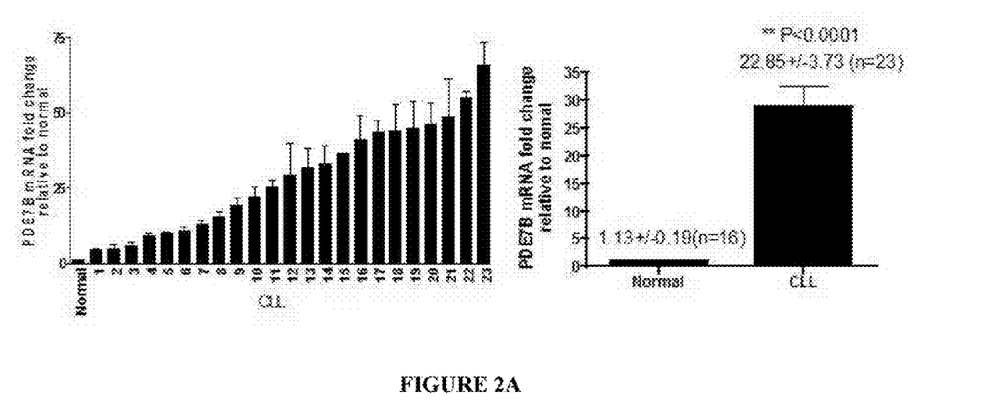
FIG. 2A shows PDE7B mRNA expression: the left panel shows each patient's PDE7B expression as fold-change relative to the mean value in normal subjects, indicating the increase in expression in CLL patients ranged from 2.9 to 95.69; the right panel shows mean+/−SE data for normal subjects and CLL patients. , $P<0.0001$ compared with normal subjects. The fold-increase for patient #294 was 254 and was not included in this figure.
Figure 5A:
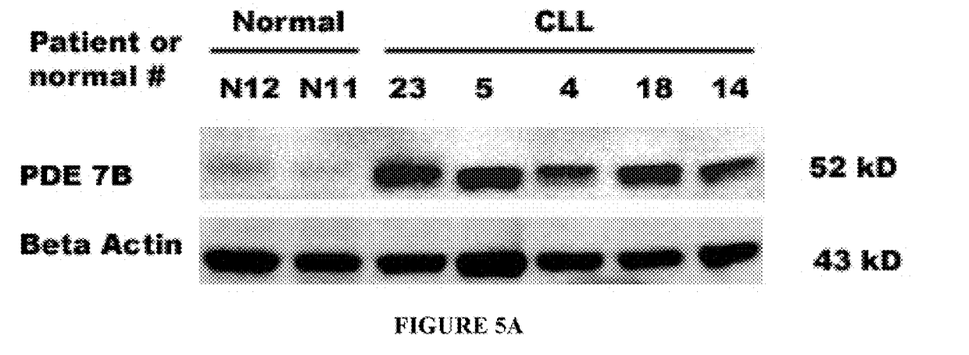
FIG. 5A shows a representative blot of PDE7B and β-actin in 2 normal subjects and 5 CLL patients.
Figure 5B:
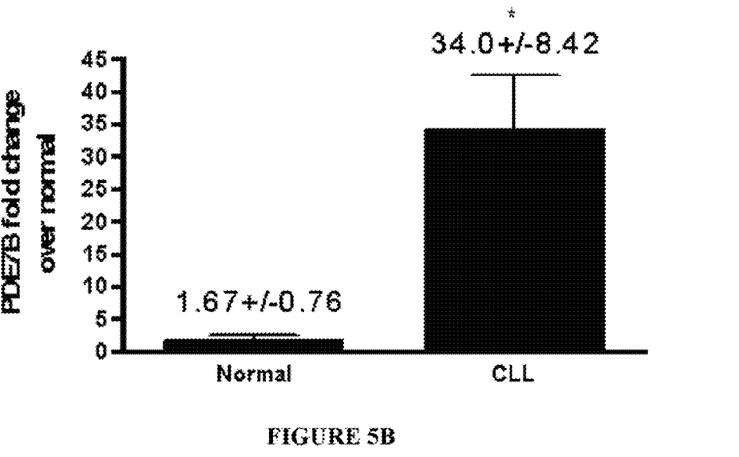
FIG. 5B represents density analysis of PDE7B protein expression in CLL PBMC (n=10) and normal PBMC (n=3, 2 other normal subjects had PDE7B protein expression levels below the levels of detection) normalized to β-actin.
Figure 5C:
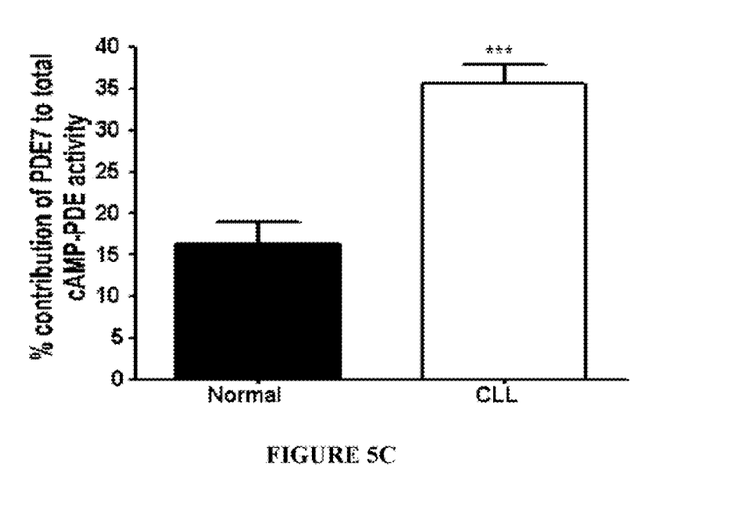
FIG. 5C shows the contribution of PDE7 to total cAMP-PDE activity as defined using BRL-50481, a PDE 7-specific inhibitor. *, $P<0.05$; ***, $P<0.0001$ compared to normal-PBMC

The mRNA expression of PDE7B in further 22 CLL-PBMC (total n=29) and 9 normal-PBMC (total n=16) was assessed using QPCR. It was found that PDE7B mRNA was increased from 2.9 to 95.7-fold (mean, 28.26±3.65, FIG. 2A) in CLL-relative to normal-PBMC. In addition to the increase in PDE mRNA expression, PDE7B protein expression was increased in CLL-PBMC compared to normal-PBMC (FIG. 5A shows a representative immunoblot). Densitometric analysis revealed ~20-fold increase in PDE7B protein expression in CLL (FIG. 5B: CLL, n=10, normal n=3, samples from 2 other normal subjects had PDE7B protein expression levels below the levels of detection). In addition, using the only commercially available specific PDE7 inhibitor, BRL-50481 [3-(N,N-dimethylsulfonamido)-4-methyl-nitrobenzene], an increased contribution of PDE7 to total cAMP-PDE activity in CLL- versus normal-PBMC was found (FIG. 5C).

Therefore, these data show that human PBMC express mRNA for many PDE isoforms, several of which are decreased with CLL (PDE2A, 3B, 4D, 5A, 8B and 9A) but mRNA expression of only PDE7B is increased. In addition, PDE7B protein expression and PDE7 enzymatic activity are increased in PBMC from patients with CLL. PDE7, which consists of PDE7A and PDE7B, is a high-affinity cAMP-PDE (Km for cAMP is <0.2 uM) with no measurable cGMP hydrolytic activity (21-23). Previous studies have shown that PDE7A is highly expressed in both human proinflammatory and immune cells, including CLL-PBMC, and is essential for the activation and proliferation of T-cells (24-28). These studies disclosed herein confirmed that PDE7A expression is high in both normal- and CLL-PBMC.

For the first time, the data presented herein show PDE7B mRNA and protein expression in these cells and that PDE7B expression although relatively low in normal-PBMC is prominently and consistently increased in CLL-PBMC. These data further implicate the increase in PDE7B expression in the increased PDE7 activity that occurs in CLL (FIG. 5C). Little is known regarding the biological role or regulation of PDE7B, other than presence of a putative phosphorylation site for PKA in its N-terminus (23). Nevertheless, based on the data presented herein, one may suggest that PDE7B regulates a pool of cAMP that is essential for cAMP-promoted apoptosis in CLL-PBMC.

Example 3

Decreased PDE3B mRNA Expression with CLL

Figure 2B:
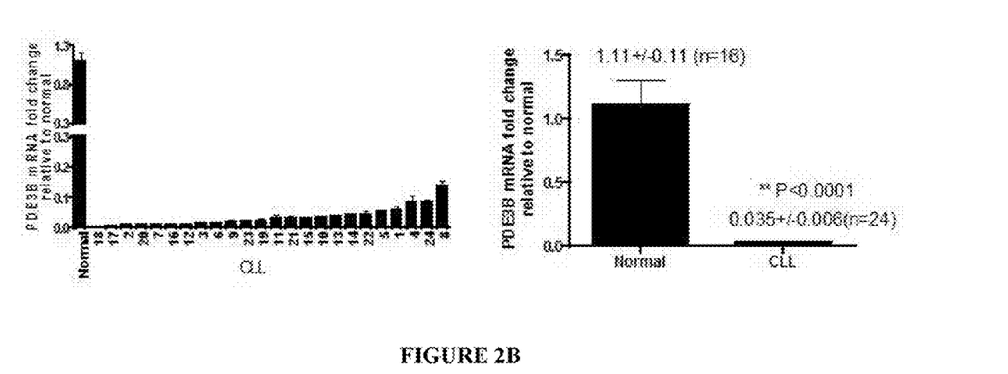
FIG. 2B shows PDE3B mRNA expression: the left panel shows each patient's PDE3B mRNA expression as fold-change relative to the mean value in normal subjects and ranged from 0.003 to 0.197; the right panel shows mean+/−SE data for normal subjects and CLL patients.  $p<0.0001$ compared with normal subjects. Cells from each CLL patient and normal subject was analyzed 3-4 separate times.

The mRNA expression of PDE3B in the same 22 CLL-PBMC (total n=29) and 9 normal-PBMC (total n=16) was also assessed using QPCR. A prominent decrease in the mRNA expression of PDE3B in CLL- relative to normal-PBMC was found (0.003 to 0.197-fold, 0.049±0.009, FIG. 2B, relative to levels in normals). PDE3B, the dominant PDE3 in lymphocytes, hydrolyzes cAMP; the cAMP hydrolytic activity of PDE3 is inhibited by cGMP, thereby integrating response to the two cyclic nucleotide (29). Consistent with the data shown herein that PDE3B expression is decreased in CLL, the PDE3 inhibitor, cilostamide, does not induce apoptosis in CLL-PBMC, implying that this PDE is not a useful therapeutic target in this disease (13). Further investigation of the transcriptional control of PDE3B may provide mechanistic insights regarding its decreased expression in CLL.

Activation of cAMP-response element-binding (CREB) proteins appears to be essential for the induction of PDE3B mRNA (30). One may suggest that the reduced cAMP and PKA activity observed in CLL (4, 5) resulting, at least in part, from the increase in PDE7B, contribute to lower PKA-mediated phosphorylation of CREB, thereby blunting CREB-mediated PDE3B transcription. Moon et al. have demonstrated that addition of a PDE4 inhibitor increases cAMP and PDE3B levels in CLL-PBMC (13). PDE3B is transcriptionally regulated by hormones, the peroxisome proliferative-activated receptor γ (PPARγ) and tumor necrosis factor-α (TNF-α) (31, 32) but whether such factors modulate PDE3B expression in CLL is not known.

Example 4

Figure 3A:
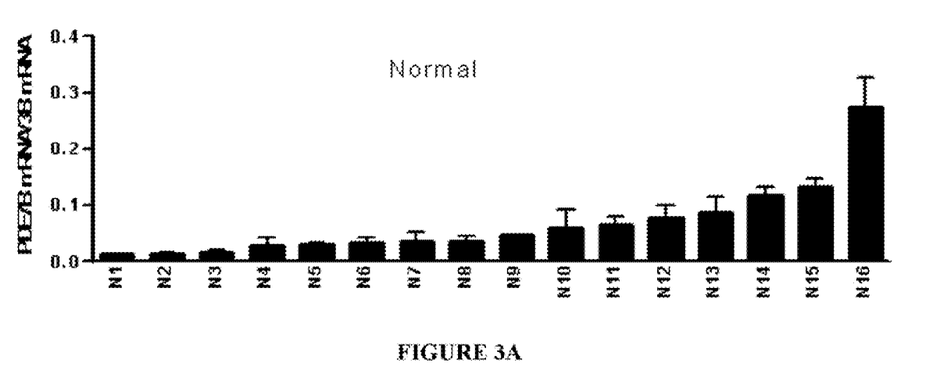
FIG. 3 illustrates that the mRNA ratio of PDE7B/3B in PBMC from CLL patients is increased compared to normal subjects and to both normal B- and non-B cells. QPCR was used to determine the mRNA expression of PDE7B and PDE3B and the ratio of the two values in CLL patients (n=29), compared to normal subjects (n=16), B-cells isolated from normal PBMC (obtained by CD 19 positive selection, n=10), and non-B cells from normal PBMC (cells remaining after CD19 positive selection). Upper panel: the mRNA ratio PDE7B/3B in normal subjects ranged from 0.01 to 0.27; Middle panel: the mRNA ratio PDE7B/3B ranged from 3.1 to 304.8 in CLL patients (analysis did not include the patient whose ratio was 1018); Lower panel: data show mean+/−SE for the mRNA ratio of PDE7B/3B of CLL, normal PBMC, non-B cells and B-cells. **, CLL- vs normal-PBMC, normal non B-cells and normal B-cells. $p<0.001$.
Figure 3B:
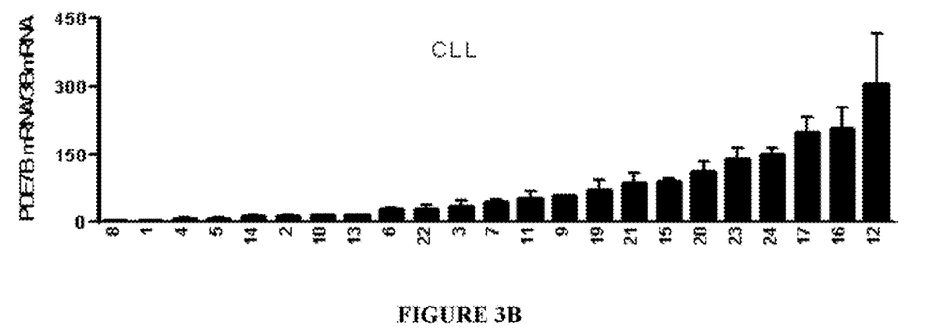
Figure 3C:
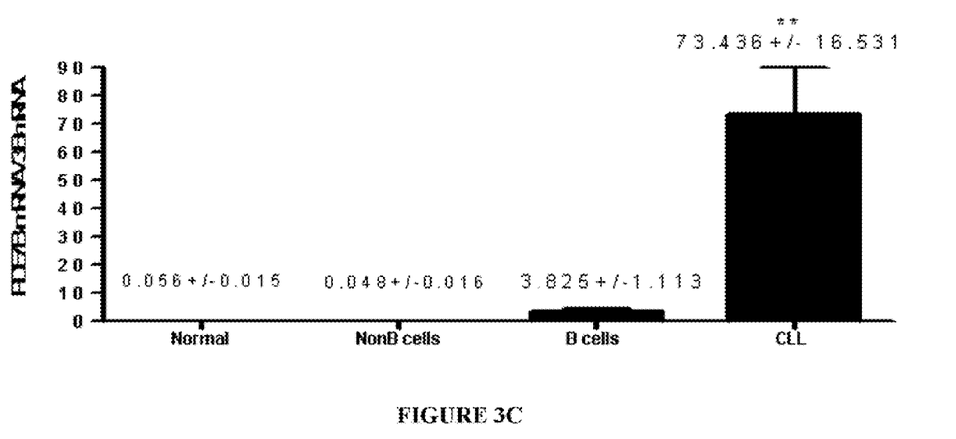

Increased mRNA Expression Ratio of PDE7B to PDE3B with CLL and its Correlation with Certain Prognostic Factors in CLL Because all patients had both higher expression levels of PDE7B and lower levels of PDE3B (FIG. 2), the ratio of the mRNA expression of PDE7B to PDE3B was calculated in order to ascertain if this ratio might provide a PDE "signature" that could serve as a biomarker for this disease. The data presented herein show that all CLL patients had a PDE7B mRNA to PDE3B mRNA ratio >3.0 (64.73±14.28, mean±SE, n=29) while all normal subjects had a ratio <0.3 (0.056±0.015, mean±SE, n=16) (FIGS. 3A-C). On average, patients with CLL thus have >1000-fold higher ratio of PDE7B mRNA/3B mRNA compared to this ratio in normal PBMC (FIG. 3C).

Because PBMC in these CLL patients are comprised of >90% B cells, mRNA expression of PDE7B and PDE3B in normal B cells (obtained from PBMC of normal subjects by CD19+ selection, yielding >90% B cells) and non-B cells (PBMC remaining after CD19+ selection) was also calculated and compared. Purified B cells yielded a PDE7B mRNA/PDE3B mRNA ratio of 3.83±1.11 (mean±SE, n=10) (FIG. 3C), a result implying that the increase PDE7B/3B mRNA ratio in PBMC-CLL partially relates to the enrichment of B-cells in CLL. However, the much higher PDE7B/PDE3B mRNA ratio with CLL suggests that other factors associated with the disease alter the expression of these two PDE isoforms. Overall, the results indicate that the mRNA ratio of PDE7B/3B in PBMC clearly discriminates CLL patients from normal subjects.

Figure 4A:
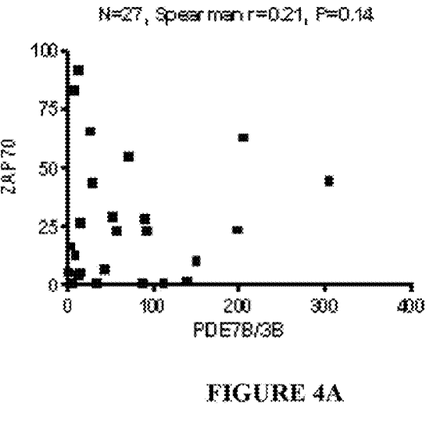
FIG. 4A: ZAP-70 (n=27, P=0.14)
Figure 4B:
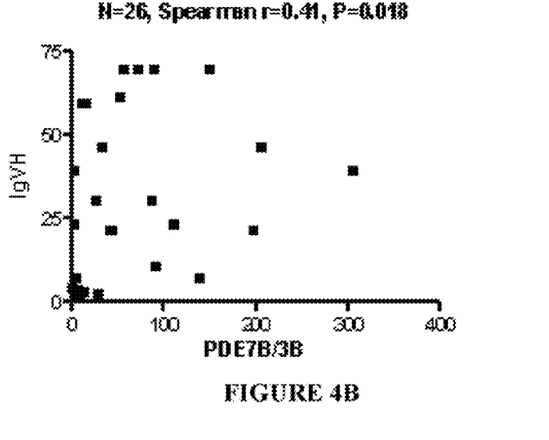
FIG. 4B: IgVH (n=21, P=0.018)
Figure 4C:
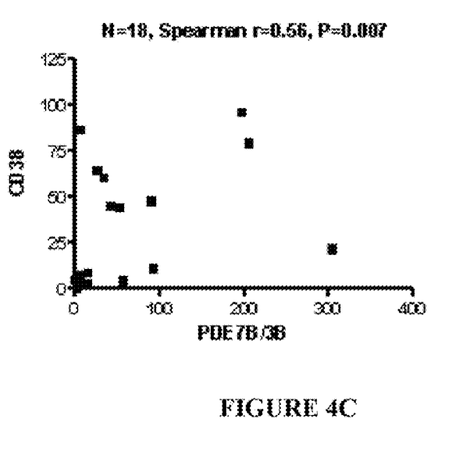
FIG. 4C: CD38 (n=18, P=0.0076)
Figure 4D:
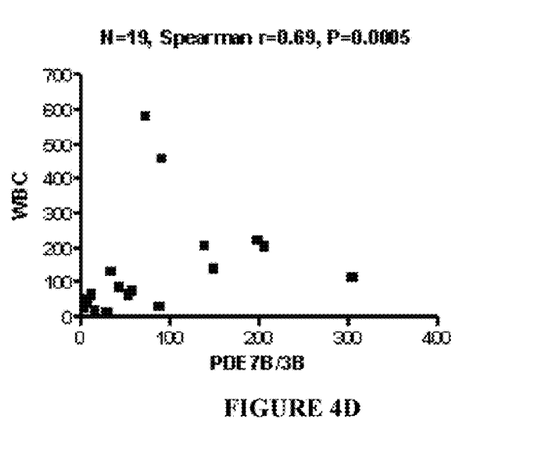
FIG. 4D: WBC (n=19, P=0.0005)
Figure 4E:
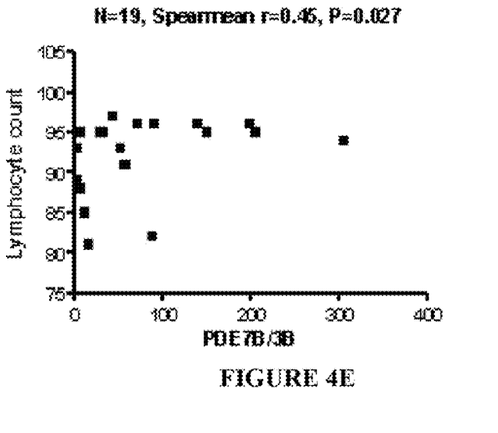
FIG. 4E: percentage lymphocyte (n=19, P=0.027).

Unmutated immunoglobulin variable heavy chain gene (IgVH), genomic aberrations (e.g., 17q and 11q deletions), age, WBC, lactate dehydrogenase (LDH), and more recently ZAP-70 and CD38 have all been identified as independent prognostic factors in CLL (19, 20). Using the one-tailed Spearman test, the relationship between the mRNA ratio of PDE7B to PDE3B and several other disease markers in CLL were assessed: ZAP-70, IgVH mutation, WBC, percentage lymphocytes, and expression of CD38 expression level (FIGS. 4A-C). The PDE7B/3B mRNA ratio did not show significant correlation with ZAP-70 (N=27, Spearman r=0.23, p=0.134) and IgVH (N=21, Spearman r=0.23, p=0.16 but did correlate with WBC (N=19, Spearman r=0.69, p=0.0005), percentage lymphocytes (N=19, Spearman r=0.449, p=0.027), and CD38 expression level (N=18, Spearman r=0.56, p=0.076).

Therefore, the altered expression of PDE7B and PDE3B not only may provide insight into events that occur with CLL but the ratio of PDE7B/3B mRNA may also be a biomarker for the disease. The increased ratio of PDE7B/3B provided herein clearly separates CLL patients from normal subjects and suggests that this ratio identifies patients with this disease; further evaluation is required to confirm if the PDE7B/3B ratio can help predict disease progression, response to treatment and prognostic information independent of other markers of CLL. Nevertheless, the studies provided herein clearly indicate that PDE7B/PDE3B mRNA appears to be a biomarker for CLL that is, is simple to obtain, requiring only use of QPCR with PDE7B and PDE3B primers.

Example 5

Figure 6A:
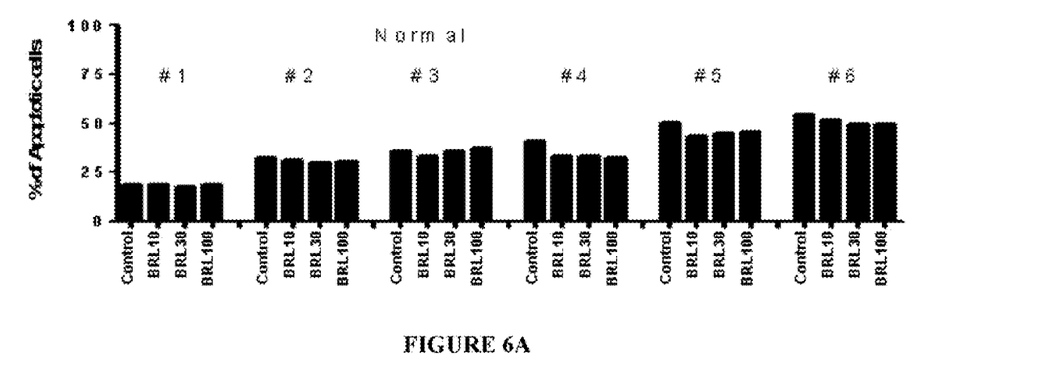
Figure 6B:
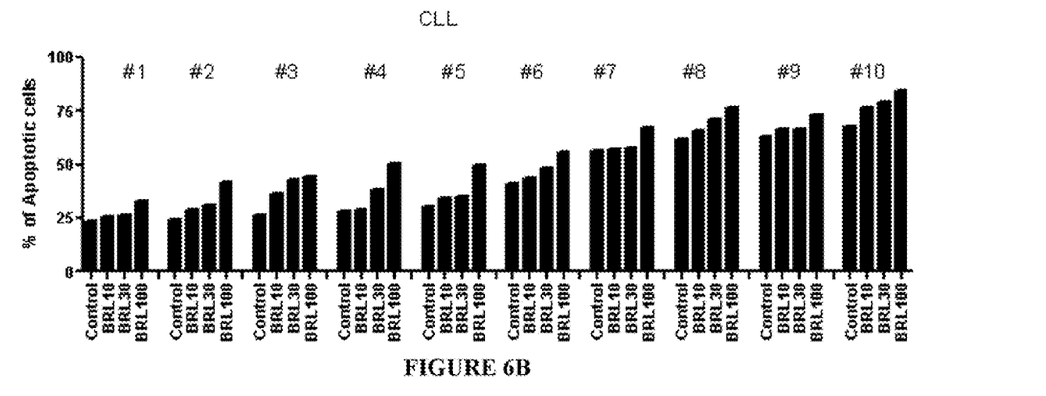
Figure 6C:
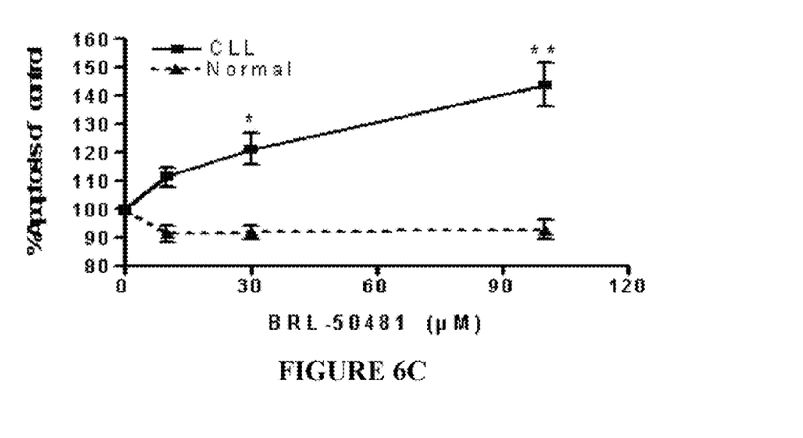

PDE7 Inhibition Induces Apoptosis in PBMC Isolated from CLL Patients but not from Normal Subjects Based on the ability of certain PDE inhibitors to induce apoptosis of lymphoid cells, and the increased mRNA and protein levels for PDE7B that were found in patients with CLL, the ability to kill CLL-PBMC of a PDE7 inhibitor, BRL-50481, was assessed. PBMC from CLL patients (n=10) and normal subjects (n=6) were grown in the absence or presence of BRL-50481 (10 µM, 30 µM and 100 µM) for 72 h. It was found that ≧30 uM BRL-54081 induced a 20-40% increase in apoptosis in CLL-PBMC but not in PBMC from normal subjects (FIG. 6A-C). Even though individual patients had different level of basal apoptosis level, BRL-50481 consistently and dose-dependently induced apoptosis in CLL-PBMC.

Therefore, a specific PDE7 inhibitor was found to dose-dependently induce apoptosis in CLL- but not normal-PBMC. Based on the cellular localization of PDE7A, it has been suggested that PDE7 inhibitors may have anti-inflammatory properties (26). Previous studies reported that the PDE7 selective inhibitor, BRL-50481 (30 µM) failed to inhibit IL-5-promoted proliferation of CD8+ T-lymphocytes and has little effect on TNFα release in either monocytes or macrophages (25). Interestingly, though, up-regulation of PDE7 in monocytes increased sensitivity to BRL-50481 (25), suggesting that a PDE7 inhibitor may be more effective in a setting such as CLL where PDE7B is increased.

Non-specific PDE and PDE4 inhibitors can promote apoptosis of CLL-PBMC and enhance the effect of cytotoxic agents (3, 8, 46), although PDE4 inhibitors have dose-limiting cardiovascular, gastrointestinal and central nervous system side effects (48). Apoptosis of CLL-PBMC by PDE4 inhibition, via a PKA-dependent pathway, leads to the upregulation of protein phosphatase 2A, dephosphorylation of BAD, mitochondrial depolarization, cytochrome c release and caspase 9 and 3 cleavage (47). Whether such mechanisms contribute to the increase apoptosis produced by BRL-50481 will require further study. Although there is ~70% identity between PDE7A and PDE7B they have unique inhibitor profiles, implying that it may be possible to find competitive inhibitors that have increased specificity for PDE7B and increased specificity for CLL (23).

In summary, the data presented herein provide evidence for altered expression of numerous PDEs in CLL, highlighting PDE7B as uniquely overexpressed with the PDE7B mRNA/3B mRNA ratio providing a potentially new diagnostic marker. The ability of a PDE7 inhibitor to promote apoptosis of CLL- but not normal-PBMC suggests that selective inhibitors of PDE7B could provide a novel therapeutic approach for the treatment of CLL. The future studies on mechanisms that produce altered PDE7B expression and PDE7 inhibitor-induced apoptosis may reveal additional information regarding both the pathophysiology and treatment of this disease.

APPENDIX A

References

1. Danilov, A. V., Danilova, O. V., Klein, A. K. & Huber, B. T. (2006) *Curr Mol Med* 6, 665-75.
2. Zhang, L. & Insel, P. A. (2004) *J Biol Chem* 279, 20858-65.
3. Tiwari, S., Dong, H., Kim, E. J., Weintraub, L., Epstein, P. M. & Lerner, A. (2005) *Biochem Pharmacol* 69, 473-83.
4. Kim, D. H. & Lerner, A. (1998) *Blood* 92, 2484-94.
5. Monahan, T. M., Marchand, N. W., Fritz, R. R. & Abell, C. W. (1975) *Cancer Res* 35, 2540-7.
6. Carpentieri, U., Monahan, T. M. & Gustavson, L. P. (1980) *J Cyclic Nucleotide Res* 6, 253-9.
7. Lugnier, C. (2006) *Pharmacol Ther* 109, 366-98.
8. Mentz, F., Merle-Beral, H., Ouaaz, F. & Binet, J. L. (1995) *Br J Haematol* 90, 957-9.
9. Mentz, F., Mossalayi, M. D., Ouaaz, F., Baudet, S., Issaly, F., Ktorza, S., Semichon, M., Binet, J. L. & Merle-Beral, H. (1996) *Blood* 88, 2:172-82.
10. Mabed, M., Aref, S., Fouda, M. & El-Sharawy, S. (2004) *Leuk Lymphoma* 45, 2029-35.
11. Willis, C. R., Goodrich, A., Park, K., Waselenko, J. K., Lucas, M., Reese, A., Diehl, L. F., Grever, M. R., Byrd, J. C. & Flinn, I. W. (2006) *Ann Hematol* 85, 301-7.
12. Lee, R., Wolda, S., Moon, E., Esselstyn, J., Hertel, C. & Lerner, A. (2002) *Cell Signal* 14, 277-84.
13. Moon, E., Lee, R., Near, R., Weintraub, L., Wolda, S. & Lerner, A. (2002) *Clin Cancer Res* 8, 589-95.
14. Siegmund, B., Welsch, J., Loher, F., Meinhardt, G., Emmerich, B., Endres, S. & Eigler, A. (2001) *Leukemia* 15, 1564-71.

15. Rassenti, L. Z., Huynh, L., Toy, T. L., Chen, L., Keating, M. J., Gribben, J. G., Neuberg, D. S., Flinn, I. W., Rai, K. R., Byrd, J. C., Kay, N. E., Greaves, A., Weiss, A. & Kipps, T. J. (2004) *N Engl J Med* 351, 893-901.
16. Murray, F., Patel, H. H., Suda, R. Y., Zhang, S., Thistlewaite, P., Yuan, J. X. & Insel, P. A. (2006) *Am J Physiol Lung Cell Mol Physiol*.
17. Thompson, W. J. & Appleman, M. M. (1971) *Biochemistry* 10, 311-6.
18. Zhang, L. & Insel, P. A. (2001) *Am J Physicol Cell Physiol* 281, C1642-7.
19. Krober, A., Seiler, T., Benner, A., Bullinger, L., Bruckle, E., Lichter, P., Dohner, H. & Stilgenbauer, S. (2002) *Blood* 100, 1410-6.
20. Deaglio, S., Vaisitti, T., Aydin, S., Ferrero, E. & Malavasi, F. (2006) *Blood* 108, 1135-44.
21. Bender, A. T. & Beavo, J. A. (2006) *Pharmacol Rev* 58, 488-520.
22. Michaeli, T., Bloom, T. J., Martins, T., Loughney, K., Ferguson, K., Riggs, M., Rodgers, L., Beavo, J. A. & Wigler, M. (1993) *J Biol Chem* 268, 12925-32.
23. Hetman, J. M., Soderling, S. H., Glavas, N. A. & Beavo, J. A. (2000) *Proc Natl Acad Sci USA* 97, 472-6.
24. Smith, S. J., Brookes-Fazakerley, S., Donnelly, L. E., Barnes, P. J., Barnette, M. S. & Giembycz, M. A. (2003) *Am J Physiol Lung Cell Mol Physiol* 284, L279-89.
25. Smith, S. J., Cieslinski, L. B., Newton, R., Donnelly, L. E., Fenwick, P. S., Nicholson, A. G., Barnes, P. J., Barnette, M. S. & Giembycz, M. A. (2004) *Mol Pharmacol* 66, 1679-89.
26. Giembycz, M. A. & Smith, S. J. (2006) *Curr Pharm Des* 12, 3207-20.
27. Li, L., Yee, C. & Beavo, J. A. (1999) *Science* 283, 848-51.
28. Gardner, C., Robas, N., Cawkill, D. & Fidock, M. (2000) *Biochem Biophys Res Commun* 272, 186-92.
29. Sheth, S. B., Chaganti, K., Bastepe, M., Ajuria, J., Brennan, K., Biradavolu, R. & Colman, R. W. (1997) *Br J Haematol* 99, 784-9.
30. Liu, H., Tang, J. R., Choi, Y. H., Napolitano, M., Hockman, S., Taira, M., Degerman, E. & Manganiello, V. C. (2006) *J Biol Chem* 281, 21096-113.
31. Ogura, T., Osawa, H., Tang, Y., Onuma, H., Ochi, M., Nishimiya, T., Kubota, N., Terauchi, Y., Kadowaki, T. & Makino, H. (2003) *FEBS Lett* 542, 65-8.
32. Rahn Landstrom, T., Mei, J., Karlsson, M., Manganiello, V. & Degerman, E. (2000) *Biochem J* 346 Pt 2, 337-43.
33. Binet, J. L., Caligaris-Cappio, F., Catovsky, D., Cheson, B., Davis, T., Dighiero, G., Dohner, H., Hallek, M., Hillmen, P., Keating, M., Montserrat, E., Kipps, T. J. & Rai, K. (2006) *Blood* 107, 859-611.
34. Byrd, J. C., Stilgenbauer, S. & Flinn, I. W. (2004) *Hematology Am Soc Hematol Educ Program*, 163-83.
35. Rai, K. R., Sawitsky, A., Cronkite, E. P., Chanana, A. D., Levy, R. N. & Pasternack, B. S. (1975) *Blood* 46, 219-34.
36. Binet, J. L., Auquier, A., Dighiero, G., Chastang, C., Piguet, H., Goasguen, J., Vaugier, G., Potron, G., Colona, P., Oberling, F., Thomas, M., Tchernia, G., Jacquillat, C., Boivin, P., Lesty, C., Duault, M. T., Monconduit, M., Belabbes, S. & Gremy, F. (1981) *Cancer* 48, 198-206.
37. Abbott, B. L. (2006) *Oncologist* 11, 21-30.
38. Saka, B., Aktan, M., Sami, U., Oner, D., Sanem, O. & Dincol, G. (2006) *Clin Lab Haematol* 28, 30-5.
39. Cochran, D. A., Evans, C. A., Blinco, D., Burthem, J., Stevenson, F. K., Gaskell, S. J. & Whetton, A. D. (2003) *Mol Cell Proteomics* 2, 1331-41.
40. Oscier, D. G., Gardiner, A. C., Mould, S. J., Glide, S., Davis, Z. A., Ibbotson, R. E., Corcoran, M. M., Chapman, R. M., Thomas, P. W., Copplestone, J. A., Orchard, J. A. & Hamblin, T. J. (2002) *Blood* 100, 1177-84.
41. Crespo, M., Bosch, F., Villamor, N., Bellosillo, B., Colomer, D., Rozman, M., Marce, S., Lopez-Guillermo, A., Campo, E. & Montserrat, E. (2003) *N Engl J Med* 348, 1764-75.
42. Del Principe, M. I., Del Poeta, G., Buccisano, F., Maurillo, L., Venditti, A., Zucchetto, A., Marini, R., Niscola, P., Consalvo, M. A., Mazzone, C., Ottaviani, L., Panetta, P., Bruno, A., Bomben, R., Suppo, G., Degan, M., Gattei, V., de Fabritiis, P., Cantonetti, M., Lo Coco, F., Del Principe, D. & Amadori, S. (2006) *Blood* 108, 853-61.
43. Hayat, A., O'Brien, D., O'Rourke, P., McGuckin, S., Fitzgerald, T., Conneally, E., Browne, P. V., McCann, S. R., Lawler, M. P. & Vandenberghe, E. (2006) *Leuk Lymphoma* 47, 2371-9.
44. Hus, I., Podhorecka, M., Bojarska-Junak, A., Rolinski, J., Schmitt, M., Sieklucka, M., Wasik-Szczepanek, E. & Dmoszynska, A. (2006) *Ann Oncol* 17, 683-90.
45. Wilhelm, C., Neubauer, A. & Brendel, C. (2006) *Cytometry B Clin Cytom* 70, 242-50.
46. Mentz, F., Merle-Beral, H. & Dalloul, A. H. (1999) *Leukemia* 13, 78-84.
47. Moon, E. Y. & Lerner, A. (2003) *Blood* 101, 4122-30.
48. Giembycz, M. A. (2001) *Expert Opin Invest Drugs* 10, 1361-79.
49. Beavo (1995) *Physiol Rev.* 75: 725-48.
50. Francis et al. (2001), *Prog Nucleic Acid Res Mol Biol.* 65:1-52.
51. Han et al. (1997) *J Biol Chem* 272 (26): 16152-57.
52. Sasaki et al. (2000) *Biochem Biophys Res Commun* 270: 575-83

What is claimed is:

1. A method for determining a prognosis of a patient with chronic lymphocytic leukemia (CLL) comprising:
    (a) obtaining a biological sample of the patient comprising lymphocytes;
    (b) determining the sample expression level of phosphodiesterase 7B (PDE7B);
    (c) comparing the expression level of PDE7B in the patient sample relative to a baseline expression level of said PDE7B; and
    (d) associating a higher relative patient PDE7B expression level with a higher risk course of CLL, thereby determining the prognosis of the patient with CLL.

2. The method of claim 1, wherein said PDE7B expression level comprises a PDE7B mRNA expression level or a PDE7B protein expression level.

3. The method of claim 2, wherein said PDE7B mRNA expression level in said patient is about 5-70 fold higher than the baseline expression level.

4. The method of claim 2, wherein said PDE7B protein expression level in said patient is about 5-90 fold higher than the baseline expression level.

5. The method of claim 1, wherein said lymphocytes comprise peripheral blood mononuclear cells (PBMCs) or B cells.

6. A kit for determining a prognosis of a patient with CLL comprising biomarker detecting reagents for detecting expression level of phosphodiesterase 7B (PDE7B) in lymphocytes from said patient, and instructions for determining the prognosis of said patient's CLL by comparing the expression level of PDE7B in the patient sample relative to a baseline expression level of said PDE7B and associating a higher relative patient PDE7B expression level with a higher risk course of CCL, thereby determining the prognosis of the patient with CLL.

7. The kit of claim 6, wherein said expression level of PDE7B comprises a PDE7B mRNA expression level or a PDE7B protein expression level.

8. The kit of claim 7, wherein said PDE7B mRNA expression level in said patient is about 5-70 fold higher than the baseline expression level.

9. The kit of claim 7, wherein said PDE7B protein expression level in said patient is about 5-90 fold higher than the baseline expression level.

10. The kit of claim 6, wherein said lymphocytes comprises peripheral blood mononuclear cells (PBMCs) or B cells.

\* \* \* \* \*